United States Patent [19]

Arfaa

[11] 4,214,583
[45] Jul. 29, 1980

[54] SURGICAL WASH SYSTEM

[76] Inventor: Manoochehr Arfaa, 202 Glenwood Ave., Bel Air, Md. 21014

[21] Appl. No.: 19,237

[22] Filed: Mar. 9, 1979

[51] Int. Cl.³ .............................................. A61M 5/00
[52] U.S. Cl. ................................................. 128/214 F
[58] Field of Search ........... 128/214 F, 214 D, 214 E, 128/DIG. 12, 226, 225, 224, 227; 222/92–95

[56] References Cited

U.S. PATENT DOCUMENTS

| | | | |
|---|---|---|---|
| 3,054,401 | 9/1962 | Gewecke | 128/214 F |
| 3,153,414 | 10/1964 | Beall et al. | 128/214 F |
| 3,228,395 | 1/1966 | Gewecke | 128/214 F |
| 3,328,255 | 6/1967 | Ilg | 128/214 D |
| 4,090,514 | 5/1978 | Hinck et al. | 128/214 F |

Primary Examiner—John D. Yasko
Attorney, Agent, or Firm—John F. McClellan, Sr.

[57] ABSTRACT

An operating room accessory for surgeons provides aseptic and closely controllable pressure wash for irrigating chest cavities, abdominal cavities, wounds and the like, in the form of a flexible-wall reservoir adapted for hanging from an I.V. support or other suitable support and having provision for hypodermic needle pressurization of the contents or administration of any medication, by insertion through a portion of the wall, and alternatively for pressure-cuff bulb pressurization; the unit includes an on-off clamp located for access by operating room assistants, and a flow control nozzle at the output for manipulation by the one operating.

7 Claims, 2 Drawing Figures

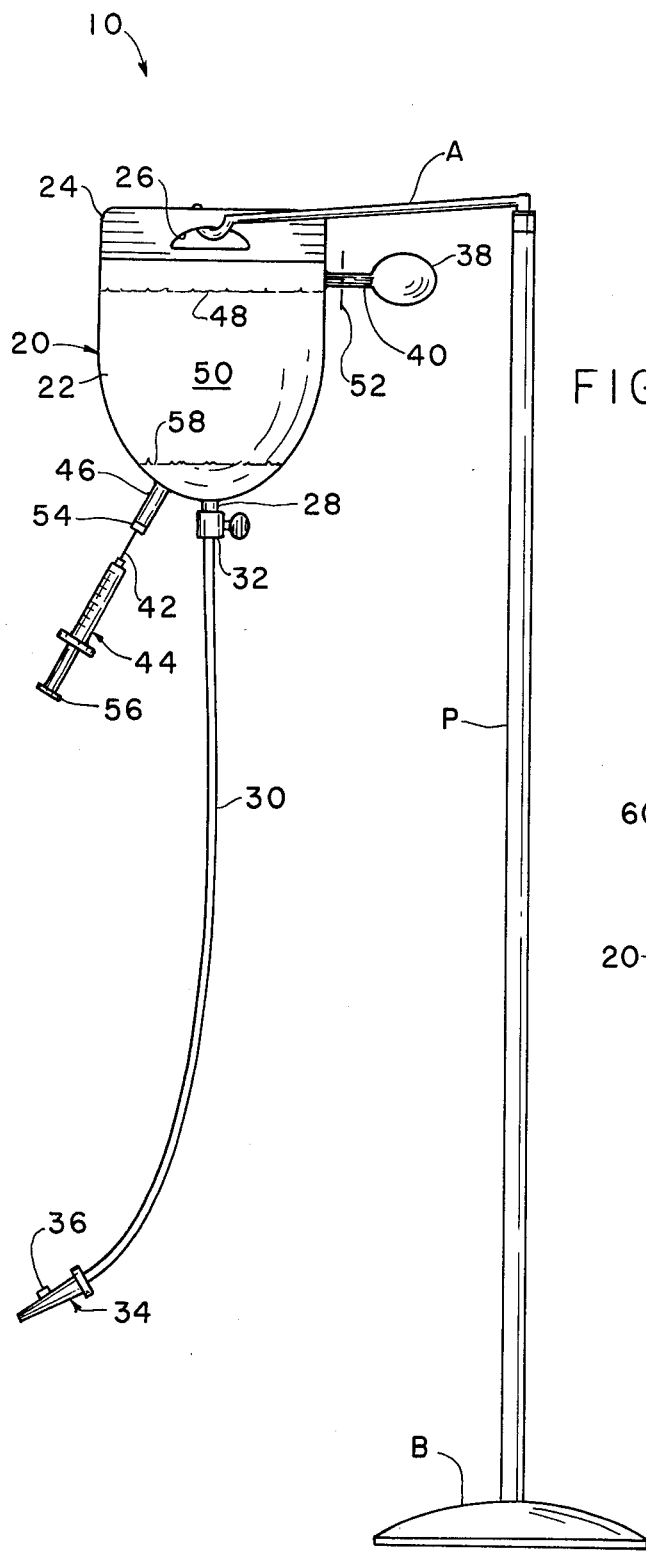
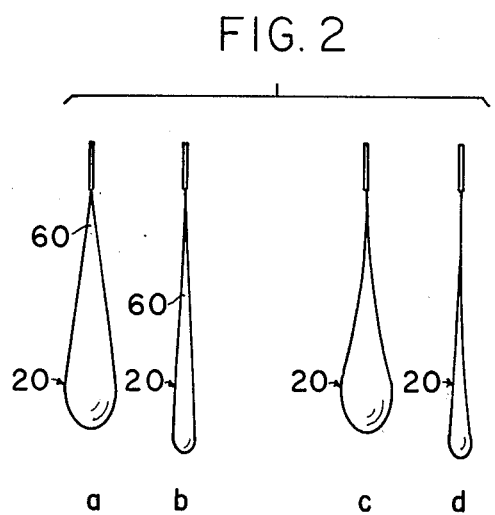

SURGICAL WASH SYSTEM

This invention relates generally to surgical wash systems and specifically to a surgical wash system having micro-control of pressure of fluid dischargeable therefrom.

Both gravity flow and pump-pressured fluid dispensing systems are known in the prior art, including valve controllable systems with flexible wall containers having flexible hose terminating in a nozzle.

However, it is believed that no known systems singly or in combination will provide the advantages of the present invention surgical wash according to the objects below set forth.

To meet conditions encountered in surgical procedures a full range of wash pressures and flow volumes is necessary.

Usually bulb syringes of limited capacity are employed for cleansing wounds; squeezing and directing these requires more attention than it should, particularly with the need for frequent refills and care to avoid excessive pressure fluctuations. Electric pump systems are expensive and are relatively inflexible in some circumstances. Sterilization of ordinary systems is a continuing and expensive problem.

Objects of the present invention therefore are to provide a wide range micro-controllable surgical wash system which is economically disposable, which requires no apparatus other than that ordinarily available in operating rooms for precise control under all conditions of demand, which is easy to learn to use and quickly deployable and usable whenever required, and which can be compactly stored in limited space in sterile condition.

Further objects are to provide a system as described which keeps the surgical field dry, neat and free of contamination by water-spillage on the field, which enables sterile introduction of selected liquid substances such as antibiotics if necessary into the wash fluid as desired, which provides facility for both micro-increase and micro-decrease of pressure without alteration of the apparatus, which is lightweight, adaptable to various size embodiments, and extremely convenient for operation by one or more people in close quarters under emergency conditions, and which is resistant to damage.

Still further objects are to exploit the inherent but unexploited advantages of conventional plastic bag and hypodermic syringe technology, in combination in the hospital operating room environment.

In brief summary given as cursive description only and not as limitation, the invention includes the combination of closed flexible wall plastic wash fluid container micro-pressurizable by use of conventional apparatus normally available in the operating room.

The above and other objects and advantages of the invention will become more readily understood on examination of the following description, including the drawings, in which like reference numerals refer to like parts:

FIG. 1 is a perspective view of the invention in use; and

FIG. 2 a, b, c and d are side elevational diagrammatic details of a container.

FIG. 1 shows embodiment 10 of the invention. Bag 20 has a lower or container portion 22 of flexible plastic construction. The bag may be of polyethylene. The upper part 24 is semi-rigid in the form of a flat plastic handle hermetically sealing closed the top of reservoir portion. Hole 26, preferably in the form of an upwardly arcuate opening centrally in the handle provides means for carrying and for hanging on the arm A of a standard I.V. pole P supported by a base B, such as may be found in any operating room.

The container has a sump connection 28 at the bottom, from which a flexible tubing or hose 30 depends. A conventional shut-off clamp 32 preferably is provided adjacent the container where it can conveniently be reached by more than one of the operating room staff, and the flexible hose terminates at a convenient distance from the container in a nozzle 34. The nozzle preferably has an on-off valve 36 of conventional design, digitally manipulable.

Improvement in this type apparatus according to this invention comprises means for pressurizing the container both for high pressure and/or high volume flow by means of a conventional pressure-cuff bulb 38 at a first connection 40 with the container interior and for micro-controllable pressurizing and flow regulation in both positive and negative increments, and for administration of medicine such as antibiotics, by the needle 42 of a conventional hypodermic syringe 44 at a similar second connection 46 with the container interior.

"Micro-control" is used here to denote a controlled quantitive amount much smaller than achievable with other commonly available equipment.

The first connection may be a simple tubular extension from the container, preferably above the level 48 of a majority of the capacity for wash fluid 50, and preferably long enough to be conventionally shut off with a pinch clamp as at line 52 when the cuff is not attached or in use.

The second connection is preferably similarly a tubular extension but with a serum-vial cap type penetrable valve 54 at the end, which may be of natural rubber conventionally cemented or clamped to the tubular extension to permit hermetic introduction of any needle 42 of hypodermic syringes of conventional size ranges for micro-pressurization or depressurization of the bag contents by manipulation of the plunger 56 of the syringe as desired. The penetrable valve and hypodermic syringe structure may be used repeatedly, the syringe being inserted and removed to prevent obstruction by it and to prevent unwanted "creep" from back-pressure, removal constituting automatic check-valve function in effect.

Preferably but not necessarily the second connection is below the level 58 of exhaustion of a substantial majority of the capacity for wash fluid and at a downward angle to the bag, as shown, so that liquid may be expelled or withdrawn efficiently by the syringe within a wide difference in volume during operation, for more positive results. For example, because the bag is flexible, it may be completely filled with liquid, so that any addition or subtraction of liquid by syringe is not set-off by elasticity of a contained gas but rather is a more positive displacement against the external atmospheric and gravitational forces shaping the contained wash liquid in the container; rate of thermal change of pressure is lowered.

FIGS. 2 a and b diagram the side elevational aspects of the container 20 in greater and lesser filled condition, respectively when containing a quantity of air or other gas 60 above the wash liquid, and FIGS. 2 c and d diagram the respective aspects when containing respectively corresponding quantities of wash fluid without the gas above.

It will be appreciated that by the above provisions any balance of air pressure and fluid pressure within the range made available by the apparatus may be obtained to establish desired flow and pressure rates.

This invention is not to be construed as limited to the particular forms disclosed herein, since these are to be regarded as illustrative rather than restrictive. It is, therefore, to be understood that the invention may be practiced within the scope of the claims otherwise than as specifically described. As example, the bag may be supplied in one or in twoo liter size, filled with sterile solution at the factory, and may be refilled by injection from a large syringe with sterile fluid, or may be discarded and a fresh bag used, as desired. In any event, quantities of sterile fluid as small as one milliliter may easily be added to or subtracted from the bag.

What is claimed and desired to be protected by United States Letters Patent is:

1. In a surgical wash system having a reservoir for hanging from a support such as an I.V. pole, flexible tubing for discharing fluid from the reservoir, means associated with the flexible tubing for controlling discharge of fluid from the reservoir including a nozzle for directing fluid discharged from the reservoir, the improvement comprising: the reservoir being a closed container having a flexible wall, and said means for controlling including micro-control means for varying the pressure within the closed container, said micro-control pressure varying means including penetrable valve structure in said flexible wall for admission of the needle of a hypodermic syringe for passage of fluid therethrough under urging of said a hypodermic syringe.

2. In a surgical wash system as recited in claim 1, the penetrable valve structure being located at a portion of the closed container below the level of a substantial majority of fluid containable in said closed container.

3. In a surgical wash system as recited in claim 2, the means for controlling further including means for pressurizing the closed container by introduction of fluid above the level of a substantial majority of fluid containable in said closed container.

4. In a surgical wash system as recited in claim 3, said means for pressurizing including a pressure cuff bulb having connection through said flexible wall of the closed container.

5. In a surgical wash system as recited in claim 4, the means for controlling further including said nozzle having a valve therein.

6. In a surgical wash system as recited in claim 5, the means for controlling including a shut-off valve in said flexible tubing adjacent the closed container.

7. In a surgical wash system as recited in claim 1, the penetrable valve structure being at a downward angle from said closed container.

* * * * *